United States Patent
Izumi et al.

(12) 
(10) Patent No.: US 6,384,218 B1
(45) Date of Patent: May 7, 2002

(54) 3,5-DIOXA-12-AZAWURTZITANE COMPOUND AND PROCESS OF PREPARING SAME

(75) Inventors: Hiroshi Izumi, c/o National Institute for Resources and Environment of 16-3, Onogawa, Tsukuba, Ibaraki-ken; Shigeru Futamura, Tsukuba, both of (JP)

(73) Assignees: Secretary of Agency of Industrial Science and Technology; Hiroshi Izumi, both of (JP)

( * ) Notice: Subject to any disclaimer, the term of this patent is extended or adjusted under 35 U.S.C. 154(b) by 0 days.

(21) Appl. No.: 09/733,063

(22) Filed: Dec. 11, 2000

(30) Foreign Application Priority Data

May 9, 2000 (JP) ........................................ 2000-135364

(51) Int. Cl.$^7$ ............................................. C07D 413/14
(52) U.S. Cl. ......................................................... 544/65
(58) Field of Search ........................................... 544/65

(56) References Cited

PUBLICATIONS

J. Org. Chem, 1999, 64, 4502–4505, Izumi et al.
J. Chem. Soc., Perkin Trans. 1, 1998, 1925–1928, Izumi et al.
Journal of the Chemical Society, Col. 1, 1998, pp. 1925–1928.
Journal of Organic Chemistry, American Chemical Society, vol. 64, 1999, pp. 4502–4505.
J. Org. Chem., vo. 62, 1997, pp. 1173–1175.
Chem. Commun., 1996, pp. 27–28.
Chemistry Letters, No. 9, 1985, Vpp. 759–760.

*Primary Examiner*—Bruck Kifle
(74) *Attorney, Agent, or Firm*—Lorusso & Loud

(57) ABSTRACT

A 3,5-dioxa-12-azawurtzitane compound represented by the formula (I) shown in the specification. The dioxaazawurtzitane compound may be prepared by reacting an amino acid, an oligo- or polypeptide or a polyamino acid with a trialdehyde represented by formula (II) shown in the specification.

3 Claims, No Drawings

3,5-DIOXA-12-AZAWURTZITANE COMPOUND AND PROCESS OF PREPARING SAME

BACKGROUND OF THE INVENTION

This invention relates to a 3,5-dioxa-12-azawurtzitane compound and a process of preparing same. The new class of dioxa-azawurtzitane compounds of the present invention have a structure similar to an amino acid or a polypeptide and will be utilizable for various applications, for example, as a molecular recognition agent for use in neurotransmission studies, an intermediate for a protein-resembling compound, a surfactant, a protective group and a host-guest complex for use as a sensor.

A dioxa-azawurtzitane of the following formula is reported by Hiroshi IZUMI and Shigeru FUTAMURA in J. Chem. Soc., Perkin Trans. 1, 1925 (1998):

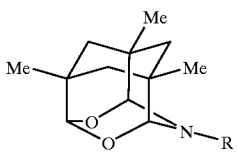

in which Me stands for a methyl group and R stands for a 4-methoxybenzyl group, a 2-(pyridin-2-yl)ethyl group or a 2-(imidazol-4-yl)ethyl group. The known wurtzitane compounds do not have a structure similar to an amino acid or a polypeptide.

SUMMARY OF THE INVENTION

It is an object of the present invention to provide a 3,5-dioxa-12-azawurtzitane compound having a structure similar to an amino acid or a polypeptide.

In accordance with one aspect of the present invention, there is provided a 3,5-dioxa-12-azawurtzitane compound represented by the following formula (I):

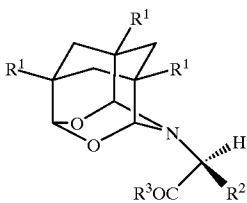

(I)

wherein $R^1$ represents an alkyl group, $R^2$ represents a group which, together with a —CH(NH$_2$)COOH group, constitutes an α-amino acid of the formula $R^2$CH(NH$_2$)COOH and which may contain one or more substituents and $R^3$ represents a hydroxyl group or a group obtained by removing a hydrogen atom of the terminal amino group of an oligo- or polypeptide or a polyamino acid.

In another aspect, the present invention provides a process of preparing a 3,5-dioxa-12-azawurtzitane compound represented by the following formula (I):

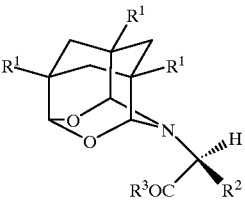

(I)

wherein $R^1$ represents an alkyl group, $R^2$ represents a group which, together with a —CH(NH$_2$)COOH group, constitutes an α-amino acid of the formula $R^2$CH(NH$_2$)COOH and which may contain one or more substituents and $R^3$ represents a hydroxyl group or a group obtained by removing a hydrogen atom of the terminal amino group of an oligo- or polypeptide or a polyamino acid, said process comprising reacting an amino acid, an oligo- or polypeptide or a polyamino acid with a trialdehyde represented by the following formula (II):

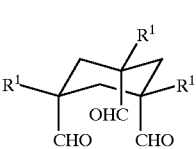

(II)

wherein $R^1$ has the same meaning as above.

In the present specification and claims, the three $R^1$s bonded to the carbon atoms at 1-, 7- and 9-positions of the 3,5-dioxa-12-azawurtzitane compound of the formula (I) or at 1-, 3- and 5-positions of the trialdehyde of the formula (II) may be the same or different alkyl groups.

Other objects, features and advantages of the present invention will be apparent from the detailed description of the preferred embodiments of the invention to follow.

DETAILED DESCRIPTION OF THE PREFERRED EMBODIMENTS OF THE INVENTION

A 3,5-dioxa-12-azawurtzitane compound of the present invention is represented by the above formula (I). In the formula (I), $R^1$ represents an alkyl group preferably having 1–12 carbon atoms. Illustrative of suitable alkyl groups of $R^1$ are methyl, ethyl, propyl, butyl, pentyl, hexyl, heptyl, octyl, nonyl, decyl and structural isomers thereof.

The symbol $R^2$ represents a group which, together with a —CH(NH$_2$)COOH group, constitutes an α-amino acid of the formula $R^2$CH(NH$_2$)COOH. Examples of the α-amino acids $R^2$CH(NH$_2$)COOH include glycine (Gly), alanine (Ala), Valine (Val), leucine (Leu), Isoleucine (Ileua), phenylalanine (Phe), tyrosine (Tyr), tryptophan (Try), serine (Ser), threonine (Thre), cystein (CySH), cystine (CyS-SCy), methionine (Meth), aspartic acid (Asp), glutamic acid (Glu), lysine (Lys), arginine (Arg) and histidine (His). The group $R^2$ may contain one or more substituents such as an alkyl group, an acetyl group, an alkoxy group, a benzoxycarbonyl group, a tert-butoxycarbonyl group, a 9-fluorenylmethoxycarbonyl group and a 1,7,9-trialkyl-3,5-dioxa-12H-azawurtzitan-12-yl group.

The symbol $R^3$ represents a hydroxyl group or a group obtained by removing a hydrogen atom of the terminal amino group of an oligo- or polypeptide or a polyamino acid.

Some examples of 3,5-dioxa-12-azawurtzitane compounds of the present invention are shown in Table 1 in which $R^1$, $R^2$ and $R^3$ are the symbols of the formula (I). The 3,5-dioxa-12-azawurtzitane compounds of the present invention, however, are of course not limited to those specifically exemplified compounds. For example, the groups $R^1$, $R^2$ and $R^3$ listed in Table 1 may be arbitrarily selected for any desired combination.

TABLE 1

| $R^1$ | $R^2$ | $R^3$ |
|---|---|---|
| $CH_3$ | H | $(His)_n$ |
| $CH_3$ | $CH_3$ | $(Gly)_n$ |
| $CH_3CH_2$ | $(CH_3)_2CH$ | $(Ala)_n$ |
| $CH_3CH_2CH_2$ | $(CH_3)_2CHCH_2$ | $(Val)_n$ |
| $CH_3(CH_2)_3$ | $CH_3CH_2(CH_3)CH$ | $(Leu)_n$ |
| $CH_3(CH_2)_4$ | ⟨phenyl⟩-$CH_2$ | $(Phe)_n$ |
| $CH_3(CH_2)_5$ | HO-⟨phenyl⟩-$CH_2$ | $(Tyr)_n$ |
| H | ⟨indolyl⟩-$CH_2$ | $(Try)_n$ |
| $(CH_3)_2CH$ | $HOCH_2$ | $(Ser)_n$ |
| $(CH_3)_3C$ | $CH_3(OH)CH$ | $(Thre)_n$ |
| $(CH_3)_2CHCH_2$ | $HSCH_2$ | $(CySH)_n$ |
| $(CH_3)_2CH(CH_2)_2$ | $HOOC(NH_2)CH$-$CH_2SSCH_2$ | $(CyS\text{—}SCy)_n$ |
| $(CH_3)_3C(CH_2)_3$ | $CH_3SCH_2CH_2$ | $(Meth)_n$ |
| $CH_3CH_2CH_2$ | $HOOCCH_2$ | $(Asp)_n$ |
| $CH_3(CH_2)_9$ | $HOOCCH_2CH_2$ | $(Glu)_n$ |
| $CH_3$ | $H_2NCH_2(CH_2)_3$ | $(Lys)_n$ |
| $CH_3$ | $HN{=}C(NH_2)NH(CH_2)_3$ | $(Arg)_n$ |
| $CH_3$ | ⟨imidazolyl⟩-$CH_2$ | OH |

In Table 1, n is an integer.

The 3,5-dioxa-12-azawurtzitane compounds of the formula (I) may be prepared by reacting a trialdehyde of the formula (II) with an amino acid, an oligo- or polypeptide or a polyamino acid. The reaction is as follows:

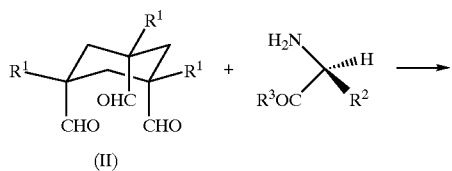

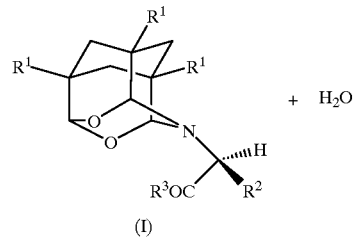

(I)

The trialdehyde of the formula (II) may be obtained by any known method such as a method described in Hiroshi IZUMI and Shigeru FUTAMURA, J. Org. Chem. vol. 64, 4502 (1999), the disclosure of which is hereby incorporated by reference herein.

The raw material to be reacted with the trialdehyde of the formula (II) may be expressed by the following formula (III):

$$(Z)_n \quad \quad (III)$$

wherein Z represents an amino acid and n is an integer of 1 or more with the proviso that, when n is two or more, the amino acids may be the same or different.

Any amino acid may be used as Z of the formula (III). Examples of amino acids include glycine (Gly), alanine (Ala), Valine (Val), leucine (Leu), Isoleucine (Ileu), phenylalanine (Phe), tyrosine (Tyr), tryptophan (Try), serine (Ser), threonine (Thre), cystein (CySH), cystine (CyS-SCy), methionine (Meth), aspartic acid (Asp), glutamic acid (Glu), lysine (Lys), arginine (Arg) and histidine (His). Any oligopeptide (composed of 2 to 9 amino acids), polypeptide (composed of 10 or more amino acids) or polyamino acid (composed of two or more same amino acids) may be used as a raw material for the above reaction.

Preferably, the reaction may be performed by mixing an aqueous solution of an amino acid, an oligo- or polypeptide or a polyamino acid with an organic polar solvent solution of the trialdehyde of the formula (II), and reacting the resulting mixture at a temperature and for a period of time sufficient to produce the desired 3,5-dioxa-12-azawurtzitane compound. The trialdehyde is generally used in a stoichiometric amount. The aqueous solution may be a buffer solution. The organic polar solvent may be an aprotic one compatible with water, such as acetone or acetonitrile. The reaction is preferably carried out at 0–70° C. for 0.5–24 hours.

The following examples will further illustrate the present invention.

EXAMPLE 1

An acetone solution containing 56 mg of a trialdehyde of the formula (II) was mixed with an aqueous solution containing 51 mg of 3-methyl-L-histidine and the mixture was reacted at room temperature for 2 hours with stirring. The crude product was extracted and purified by chromatography to obtain 90 mg (yield: 94%) of 3,5-dioxa-12-azawurtzitane compound of the formula (I) in which $R^1$ is a methyl group, $R^2$ is a (1-methylimidazol-4-yl)methyl group and $R^3$ is a hydroxyl group. The results of the NMR analysis of the product are shown below.

$^1$H NMR (acetone-$d_6$): δ60.78 (d, 1H, J=11.9 Hz, methylene H), 0.89 (d, 2H, J=12.1 Hz, methylene H), 0.95 (s, 3H, methyl H), 0.99 (s, 3H, methyl H), 1.01 (s, 3H, methyl H), 1.33 (d, 2H, J=12.1 Hz, methylene H), 1.43 (d, 1H, J=11.9

Hz, methylene H), 3.15 (dd, 1H, J=15.5 Hz, J=9.3 Hz, methylene H), 3.35 (dd, 1H, J=15.5 Hz, J=4.5 Hz, methylene H), 3.65 (s, 3H, imidazole methyl H), 4.24 (dd, 1H, J=9.3 Hz, J=4.5 Hz, methine H), 4.34 (s, 1H, wurtzitane methine H), 4.46 (s, 1H, wurtzitane methine H), 4.74 (s, 1H, wurtzitane methine H), 6.76 (s, 1H, imidazole H), 7.38 (s, 1H, imidazole H).

EXAMPLE 2

An acetone solution containing 10 mg of a trialdehyde of the formula (II) was mixed with an aqueous solution containing 14 mg of a peptide Gly-Gly-His and the mixture was reacted at room temperature for 2 hours with stirring. The crude product was extracted and purified by chromatography to obtain 17 mg (yield: 82%) of 3,5-dioxa-12-azawurtzitane compound of the formula (I) in which $R^1$ is a methyl group, $R^2$ is a hydrogen atom and $R^3$ is a Gly-His residue. The results of the NMR analysis of the product are shown below.

$^1$H NMR (acetone-$d_6$/$D_2O$): δ60.75 (d, 1H, J=12.2 Hz, methylene H), 0.81 (d, 2H, J=11.6 Hz, methylene H), 0.90 (s, 3H, methyl H), 0.94 (s, 3H, methyl H), 0.94 (s, 3H, methyl H), 1.23 (d, 2H, J=11.6 Hz, methylene H), 1.57 (d, 1H, J=12.2 Hz, methylene H), 3.00 (dd, 1H, J=15.3 Hz, J=7.3 Hz, methylene H), 3.16 (dd, 1H, J=15.3 Hz, J=4.9 Hz, methylene H), 3.71 (d, AB, 1H, J=17.1 Hz, methylene H), 3.77 (d, AB, 1H, J=17.1 Hz, methylene H), 3.86 (d, AB, 1H, J=16.9 Hz, methylene H), 3.91 (d, AB, 1H, J=16.9 Hz, methylene H), 4.06 (s, 1H, wurtzitane methine H), 4.08 (s, 1H, wurtzitane methine H), 4.37 (dd, 1H, J=7.3 Hz, J=4.9 Hz, methine H), 4.69 (s, 1H, wurtzitane methine H), 7.16 (s, 1H, imidazole H), 8.41 (s, 1H, imidazole H).

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A 3,5-dioxa-12-azawurtzitane compound represented by the following formula (I):

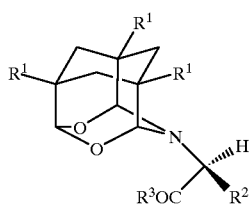

(I)

wherein $R^3$ represents an alkyl group, $R^2$ is selected from the group consisting of hydrogen, the following members:

CH$_3$—
(CH$_3$)$_2$CH—
(CH$_3$)$_2$CHCH$_2$—
CH$_3$CH$_2$CH(CH$_3$)—
PhCH$_2$—
HOPhCH$_2$—

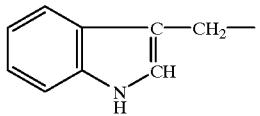

HOCH$_2$—
CH$_3$CH(OH)—
HSCH$_2$—
COOHCH(NH$_2$)CH$_2$S—SCH$_2$—
CH$_3$S(CH$_2$)$_2$—
COOHCH$_2$—
HOOC(CH$_2$)$_2$—
NH$_2$CH$_2$(CH$_2$)$_3$—
NH$_2$NHC(NM(CH$_2$)$_3$—

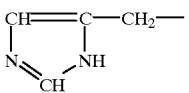

and said members substituted with one or more of alkyl, acetyl, alkoxy, benzoxycarbonyl, tert-butoxycarbonyl, 9-fluorenylmethoxycarbonyl, and 1,7,9-trialkyl-3,5-dioxa-12H-azawurtzitan-12-yl, and $R^3$ is selected from the group consisting of hydroxyl, oligopeptides, polypeptides and polyamino acids, provided that where $R^3$ is an oligopeptide, polypeptide or polyamino acid it is linked through a terminal amino group.

2. A process of preparing a 3,5-dioxa-12-azawurtzitane compound represented by the following formula (I):

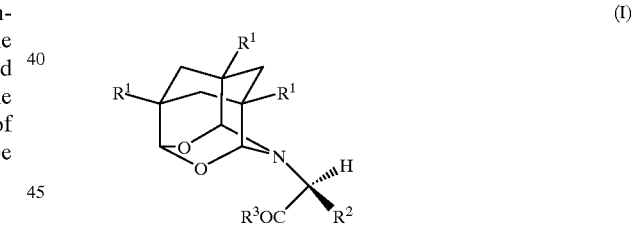

(I)

wherein $R^1$ represents an alkyl group, $R^2$ is selected from the group consisting of hydrogen, the following members:

CH$_3$—
(CH$_3$)$_2$CH—
(CH$_3$)$_2$CHCH$_2$—
CH$_3$CH$_2$CH(CH$_3$)—
PhCH$_2$—
HOPhCH$_2$—

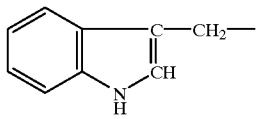

HOCH$_2$—
CH$_3$CH(OH)—
HSCH$_2$—

COOHCH(NH$_2$)CH$_2$S—SCH$_2$—
CH$_3$S(CH$_2$)$_2$—
COOHCH$_2$—
HOOC(CH$_2$)$_2$—
NH$_2$CH$_2$(CH$_2$)$_3$—
NH$_2$NHC(NH)(CH$_2$)$_3$—

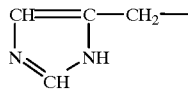

3. A process as claimed in claim 2, comprising mixing an aqueous solution of said amino acid, an oligo- or polypeptide or a polyamino acid with an organic polar solvent solution of said trialdehyde, and reacting the resulting mixture at a temperature and for a period of time sufficient to obtain said 3,5-dioxa-12-azawurtzitane compound. and said members substituted with one or more of alkyl, acetyl, alkoxy, benzoxycarbonyl, tert-butoxycarbonyl, 9-fluorenylmethoxycarbonyl and 1,7,9-trialkyl-3,5-dioxa-12H-azawurtzitan-12-yl, and R$^3$ is selected from the group consisting of hydroxyl, oligopeptides, polypeptides and polyamino acids, provided that where R$^3$ is an oligopeptide, a polypeptide or a polyamino acid, it is linked through a terminal amino group represents a hydroxyl group or a group obtained by removing a hydrogen atom of the terminal amino group of an oligo- or polypeptide or a polyamino acid, said process comprising reacting an amino acid, an oligo- or polypeptide or a polyamino acid with a trialdehyde represented by the following formula (II):

(II)

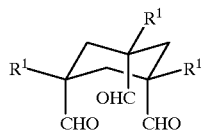

wherein R$^1$ has the same meaning as above.

* * * * *

UNITED STATES PATENT AND TRADEMARK OFFICE
CERTIFICATE OF CORRECTION

PATENT NO. : 6,384,218 B1
DATED : May 7, 2002
INVENTOR(S) : Izumi et al.

It is certified that error appears in the above-identified patent and that said Letters Patent is hereby corrected as shown below:

Column 4,
Line 64, "60.78" should read -- 0.78 --

Column 5,
Line 22, "60.75" should read -- 0.75 --

Columns 7 and 8,
Which read: "
COOHCH(NH$_2$)CH$_2$S—SCH$_2$—
CH$_3$S(CH$_2$)$_2$—
COOHCH$_2$—
HOOC(CH$_2$)$_2$—
NH$_2$CH$_2$(CH$_2$)$_3$—
NH$_2$NHC(NH)(CH$_2$)$_3$—

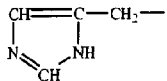

3. A process as claimed in claim 2, comprising mixing an aqueous solution of said amino acid, an oligo- or polypeptide or a polyamino acid with an organic polar solvent solution of said trialdehyde, and reacting the resulting mixture at a temperature and for a period of time sufficient to obtain said 3,5-dioxa-12-azawurtzitane compound. and said members substituted with one or more of alkyl, acetyl, alkoxy, benzoxycarbonyl, tertbutoxycarbonyl, 9-fluorenylmethoxycarbonyl and 1,7,9-trialkyl-3,5-dioxa-12Hazawurtzitan-12-yl, and $R^3$ is selected from the group consisting of hydroxyl, oligopeptides, polypeptides polyamino acids, provided that where $R^3$ is an oligopeptide, a polypeptide or a polyamino acid, it is linked through a terminal amino group represents a hydroxyl group or a group obtained by removing a hydrogen atom of the terminal amino group of an oligo- or polypeptide or a polyamino acid, said process comprising reacting an amino acid, an oligo- or polypeptide or a polyamino acid with a trialdehyde represented by the following formula (II):

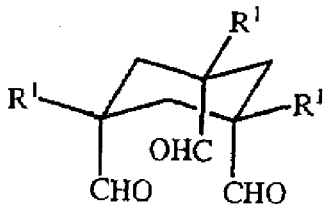

UNITED STATES PATENT AND TRADEMARK OFFICE
CERTIFICATE OF CORRECTION

PATENT NO. : 6,384,218 B1
DATED : May 7, 2002
INVENTOR(S) : Izumi et al.

It is certified that error appears in the above-identified patent and that said Letters Patent is hereby corrected as shown below:

wherein R1 has the same meaning as above."

Should read: -- $COOHCH(NH_2)CH_2S-SCH_2-$
$CH_3S(CH_2)_2-$
$COOHCH_2-$
$HOOC(CH_2)_2-$
$NH_2CH_2(CH_2)_3-$
$NH_2NHC(NH)(CH_2)_3-$

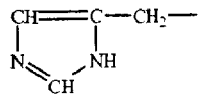

-- and said members substituted with one or more of alkyl, acetyl, alkoxy, benzoxycarbonyl, tert-butoxycarbonyl, 9-fluorenylmethoxycarbonyl and 1,7,9-trialkyl-3,5-dioxa-12Hazawurtzitane-12-yl, and $R^3$ is selected from the group consisting of hydroxyl, oligopeptides, polypeptides polyamino acids, provided that where $R^3$ is an oligopeptide, a polypeptide or a polyamino acid, it is linked through a terminal amino group represents a hydroxyl group or a group obtained by removing a hydrogen atom of the terminal amino group of an oligo- or polypeptide or a polyamino acid, said process comprising reacting an amino acid, an oligo- or polypeptide or a polyamino acid with a trialdehyde represented by the following formula (II):

--

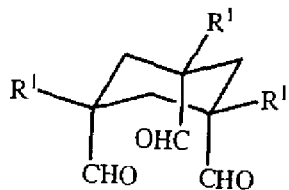

-- wherein R1 has the same meaning as above.

UNITED STATES PATENT AND TRADEMARK OFFICE
CERTIFICATE OF CORRECTION

PATENT NO. : 6,384,218 B1
DATED : May 7, 2002
INVENTOR(S) : Izumi et al.

It is certified that error appears in the above-identified patent and that said Letters Patent is hereby corrected as shown below:

3. A process as claimed in claim 2, comprising mixing an aqueous solution of said amino acid, an oligo- or polypeptide or a polyamino acid with an organic polar solvent solution of said trialdehyde, and reacting the resulting mixture at a temperature and for a period of time sufficient to obtain said 3,5-dioxa-12-azawurtzitane compound. --

Signed and Sealed this

Eighth Day of October, 2002

*Attest:*

JAMES E. ROGAN
*Director of the United States Patent and Trademark Office*

*Attesting Officer*